United States Patent
Knopp

(10) Patent No.: US 9,965,874 B2
(45) Date of Patent: May 8, 2018

(54) CALIBRATION METHOD FOR AN MPI(=MAGNETIC PARTICLE IMAGING) APPARATUS

(71) Applicant: BRUKER BIOSPIN MRI GMBH, Ettingen (DE)

(72) Inventor: Tobias Knopp, Waldbronn (DE)

(73) Assignee: Bruker BioSpin MRI GmbH, Ettlingen (DE)

( * ) Notice: Subject to any disclaimer, the term of this patent is extended or adjusted under 35 U.S.C. 154(b) by 667 days.

(21) Appl. No.: 14/409,477

(22) PCT Filed: Nov. 14, 2012

(86) PCT No.: PCT/EP2012/072550
§ 371 (c)(1),
(2) Date: Apr. 13, 2015

(87) PCT Pub. No.: WO2014/005658
PCT Pub. Date: Jan. 9, 2014

(65) Prior Publication Data
US 2015/0221103 A1  Aug. 6, 2015

(30) Foreign Application Priority Data

Jul. 4, 2012  (DE) .................. 10 2012 211 662

(51) Int. Cl.
| | |
|---|---|
| *G06T 11/00* | (2006.01) |
| *G01R 33/58* | (2006.01) |
| *G01R 33/12* | (2006.01) |
| *G01R 33/00* | (2006.01) |
| *A61B 5/05* | (2006.01) |
| *H03M 7/30* | (2006.01) |

(52) U.S. Cl.
CPC ........ *G06T 11/005* (2013.01); *G01R 33/0023* (2013.01); *G01R 33/1276* (2013.01); *A61B 5/0515* (2013.01); *H03M 7/3062* (2013.01)

(58) Field of Classification Search
CPC ........... G01R 33/0017; G01R 33/0023; G01R 33/1276; G01R 33/5601; G01R 33/58; A61B 5/0515; G06T 11/005
See application file for complete search history.

(56) References Cited

U.S. PATENT DOCUMENTS

| | | | |
|---|---|---|---|
| 2011/0221438 A1 | 9/2011 | Goodwill et al. | ............ 324/301 |
| 2011/0316526 A1* | 12/2011 | Nisato et al. | ................. 324/202 |
| 2017/0020407 A1* | 1/2017 | Weber | ................. A61B 5/0515 |

OTHER PUBLICATIONS

J. Weizenecker et al., "Three-dimensional real-time in vivo magnetic particle imaging", Phys. Med. Biol. 54 (2009) L1-L10.
Aleksi Halkola et al., "System Calibration Unit for Magnetic Particle Imaging: Focus Field Based System Function", Magnetic Particle Imaging, SPPHY 140, pp. 27-31. Springer-Verlag Berlin Heidelberg 2012.
Emmanuel J. Candes et al., "An Introduction to Compressive Sampling", IEEE Signal Processing Magazine (21) Mar. 2008.
Tobias Knopp et al., "Model-Based Reconstruction for Magnetic Particle Imaging", IEEE Transactions on Medical Imaging, vol. 29, No. 1, Jan. 2010.
Patrick W. Goodwill et al., "Projection X-Space Magnetic Particle Imaging", IEEE Transactions on Medical Imaging, vol. 31, No. 5, May 2012.
Juergen Rahmer et al., "Signal encoding in magnetic particle imaging: properties of the system function", 1. Apr. 2009, BMC Medical Imaging 2009, vol. 9:4.
Michael Lustig et al., "Sparse MRI: The Application of Compressed Sensing for Rapid MR Imaging", Magnetic Resonance in Medicine 58:1182-1195 (2007).
J. Lampe et al., "Fast reconstruction in magnetic particle imaging", Phys. Med. Biol. 57 (2012) Pa. 1113-1134.
G. Hosein Mohimani et al., "A fast approach for overcomplete sparse decomposition based on smoothed 1° norm". IEEE Transactions on Signal Processing, vol. XX, No. Y, Month 2007.
Amir Beck et al., "A Fast Iterative Shrinkage-Thresholding Algorithm for Linear Inverse Problems", Siam J. Imaging Sciences, vol. 2, No. 1, pp. 183-202, 2009.
Patrick W. Goodwill et al., "Multidimensional X-Space Magnetic Particle Imaging", IEEE Trans Med Imaging, Sep. 2011; 30(9): Pa. 1581-1590. doi:10.1109/TMI.2011.2125982. Sep. 2011.

* cited by examiner

*Primary Examiner* — Andrew W Johns
(74) *Attorney, Agent, or Firm* — Paul Vincent

(57) ABSTRACT

A calibration method for an MPI (=magnetic particle imaging) apparatus for conducting an MPI experiment, wherein the calibration method comprises m calibration MPI measurements with a calibration test piece and uses these measurements to create an image reconstruction matrix with which the signal contributions of N voxels within an investigation volume of the MPI apparatus are determined, wherein compressed sensing steps are applied in the calibration method with a transformation matrix that sparsifies the image construction matrix, and wherein only a number M<N of calibration MPI measurements for M voxels are carried out, from which the image reconstruction matrix is created and stored. This specifies an efficient method for determination of the system matrix for the MPI imaging method, which does not require much time to determine an MPI system function and nevertheless achieves a high degree of precision.

12 Claims, 3 Drawing Sheets

CALIBRATION METHOD FOR AN MPI(=MAGNETIC PARTICLE IMAGING) APPARATUS

BACKGROUND OF THE INVENTION

The invention concerns a calibration method for an MPI apparatus to perform an MPI experiment, wherein the calibration method comprises M calibration MPI measurements with a calibration sample and uses these measurements to create an image reconstruction matrix with which the signal contributions of N voxels within a volume under investigation of the MPI apparatus are determined.

A method of this type is disclosed e.g. by references [WGR09] or [KSB10].

Magnetic particle imaging (abbreviation "MPI") is a new imaging method that allows to determine the spatial distribution of magnetic nanoparticles [WGR09]. For this purpose, the particles are exposed to different static and dynamic magnetic fields and the changes in magnetization of the particles are detected using receiver coils. MPI utilizes a magnetic gradient field that has a field-free point (FFP) for spatial encoding. Shifting the FFP along a pre-defined trajectory allows scanning of the measurement range to be investigated, thereby using dynamic excitation fields (drive fields).

The correlation between the particle distribution to be reconstructed c(r) and the spectral coefficients of the measuring signal $\hat{u}_k$ k=0, ..., K−1 can be described by a linear integral equation $$\hat{u}_k = \int_{Object} c(r) s_k(r) d^3 r \qquad (1)$$

$s_k(r)$ thereby describes the system function which depends both on the location r and also on the frequency index k. The number of available frequencies K depends on the time resolution of the measurement hardware and on the utilized measurement trajectory.

There are different methods for determining the system function, which are either based on a model of the MPI signal chain or on a calibration measurement. In the standard method used up to now, a small sample filled with particles (calibration sample) in the form of an image voxel is used. When the sample is positioned at a position r' and a measurement $\hat{u}_k'$ is subsequently recorded using the MPI system, the system function at this location can be approximated by $$s_k(r') \approx \frac{\hat{u}_k'}{V_0 c_0} \qquad (2)$$

$V_0$ designates the volume and $c_0$ designates the particle concentration of the calibration sample. The smaller the calibration sample the better the approximation. Recording of the system function at all positions in the measurement range requires movement of the calibration sample by means of a positioning robot. The calibration sample is thereby alternately moved to the subsequent position followed by measurement recording using the MPI system. Normally a Cartesian grid with spatial points $r_n$, n=0, ..., N−1 is used. N thereby designates the overall number of scanning points.

After discretization of the equation system (1) at points $r_n$, n=0, ..., N−1, one obtains a linear equation system $$\hat{u} = Sc, \qquad (3)$$

which is to be solved in order to reconstruct the MPI measurement data. During calibration measurement, the system matrix is measured in columns. The n-th calibration measurement is multiplied by a factor of $1/(V_0 c_0)$ and entered in the n-th column of the system matrix.

The above described method for determining the system function is advantageous in that it can determine the actual physical processes during an MPI experiment. This method, however, is disadvantageous in that certain parts of the system function determined in this fashion may be noisy, since an MPI measurement basically contains noise. One even more substantial disadvantage, however, is the time expenditure of the method. In [WGR09], the determination of a 3D system function on a coarse grid of a size of 34×20×28, which covers a measuring field of 20.4×12×16.8 $mm^3$, required approximately 6 hours. On a finer grid, the determination of the system function would require days to months, which is not applicable in practice.

[KSB10] discloses an alternative method. This method utilizes a model of the MPI signal chain instead of a complex calibration measurement. The method is much faster, but is disadvantageous, since it does not achieve the accuracy of the measured system function, which is mainly due to the fact that up to now, nobody has found a particle model that describes the physical behavior of the particles with sufficiently precision.

It is not necessary for the size of the calibration sample and the size of an image voxel to coincide. It may e.g. be reasonable to use a larger calibration sample in order to improve the signal-to-noise ratio of the measurement data, which might, however, be accompanied by a loss in resolution. [HBRGB12] discloses a calibration method, in which the mechanical motion of the point sample is replaced by electromagnetic motion of the magnetic fields. For this purpose, the calibration sample is positioned at a fixed location. Subsequently, the same static magnetic field that prevails at the voxel positions in the measuring field to be measured, is successively generated at the location of the calibration sample. This accelerates the calibration measurement, since an electromagnetic field change can be realized more quickly than mechanical movement of the calibration sample. The method proposed in this invention does not depend on whether the calibration data is recorded by mechanical or electromagnetic steps.

While in [WGR09] the overall measuring volume is covered by the measurement trajectory, in case of larger MPI scanners (e.g. for applications on human beings) only a small area of the overall measuring volume (patient volume) may be covered by varying the excitation field. In this case, a multi-station approach can be used, in which small subvolumes are successively scanned. In this case, a dedicated system matrix must be recorded for each subvolume. The method proposed in this invention can be applied for any subvolume in this case.

Departing therefrom, it is the underlying purpose of the present invention to specify a more efficient method for determining the system matrix for the imaging MPI method, which determines an MPI system function within a short time, thereby nevertheless achieving high accuracy.

SUMMARY OF THE INVENTION

In accordance with the invention, this object is achieved in a surprisingly simple but effective fashion in that the calibration method applies compressed sensing steps with a transformation matrix which sparsifies the image reconstruction matrix, wherein the transformation matrix comprises analytic transformations, a modelled MPI-system matrix, a simulated or a measured system matrix and only a number of M<N calibration MPI measurements for M voxels are performed, wherein the M voxels from which the image reconstruction matrix is created and stored are selected in a random or pseudo-random fashion.

The inventive method is based on the findings that the MPI system function is extremely easy to condense. As is illustrated in [Lam12], each line of the MPI system matrix may be illustrated by a base transformation in the form of $$s_k = B v_k \quad (4)$$

$s_k$ thereby designates the k-th line of the system matrix S. $v_k$ moreover describes the coefficient vector for illustrating the k-th line in the base B. With suitable selection of the base transformation, the coefficient vector contains only very few non-zero entries. The majority of the coefficients is exactly zero or has a negligibly small value such that these coefficients can be removed with good approximation. One application of the development of a system function in base functions consists in condensing the system function, which substantially reduces the reconstruction time. For this purpose, the system function is initially determined with high resolution and subsequently transferred to the sparse space of the base functions [Lam12]. This method, however, does not solve the problem of fast determination of the system function.

The present invention proposes the use of a method which is known per se from literature as compressed sensing (see for example [BT09] or the publication Candes, E. J.; Ecole Polytech., Paris; Wakin, M. B.: "An Introduction To Compressive Sampling", Signal Processing Magazine, IEEE (Volume 25, Issue 2)) in another context in order to determine the coefficients $v_k$ already with only a few MPI calibration measurements. The calibration measurements for this purpose are determined at M<<N positions $r_m$, m=0, ..., M−1 and are stored as a matrix with line vectors $y_k$. $y_k$ can be represented by means of a reduced base transformation matrix $B_r$ $$y_k = B_r v_k \quad (5)$$

Since this equation system is highly under-determined, it has an infinite number of solutions. In order to nevertheless determine the coefficient vector $v_k$, compressed sensing algorithms benefit from the fact that the solution to be determined has only a few non-zero entries. In addition to the sparsity of the solution, these algorithms require an incoherent transformation matrix $B_r$. This can be achieved by selecting the scanning points $r_m$, m=0, ..., M−1 randomly or pseudo-randomly.

With the previous knowledge that the searched coefficients are sparse, they can nevertheless be determined with the following approach:

Minimize $\|v_k\|$ under the secondary condition
$y_k = B_r v_k$. (6)

In this connection, the norm can be selected differently. For example, the norms $\|v_k\|_0$ or $\|v_k\|_1$ may be used, wherein usually the l1 norm is used. Since the calibration measurements $y_m$ are possibly noisy, the approach Minimize $\|v_k\|$ under the side condition $\|y_k - B_r v_k\|_2 < \epsilon$ (7)

can improve the results. In this connection, the parameter $\epsilon$ allows a certain deviation between the measured data and the calculated solution. For generally solving the problems (6) and (7), a large number of algorithms were developed. Some of the most efficient algorithms are the SLO algorithm [HMC09] and the FISTA algorithm [BT09].

Further advantages of the invention can be extracted from the description and the drawing. The features mentioned above and below may be used in accordance with the invention either individually or collectively in arbitrary combination. The data of the illustrated and described embodiment are not to be understood as an exhaustive enumeration, rather have exemplary character for describing the invention.

DESCRIPTION OF THE PREFERRED EMBODIMENT

Figure 1:
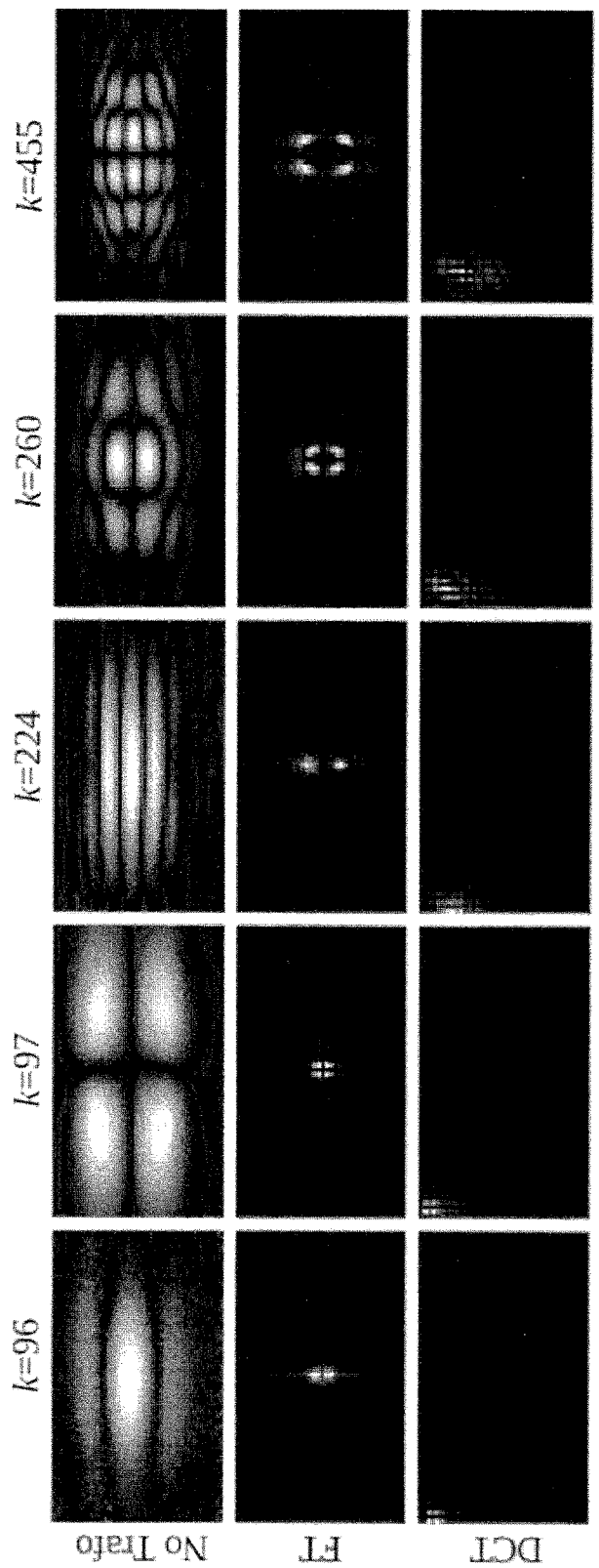
FIG. 1 shows five selected lines of the MPI system matrix prior to and after application of a base transformation (4). DFT and DCT were used as transformations. As can be seen, the transformed MPI system matrix lines are different from zero at only a few points.
Figure 2:
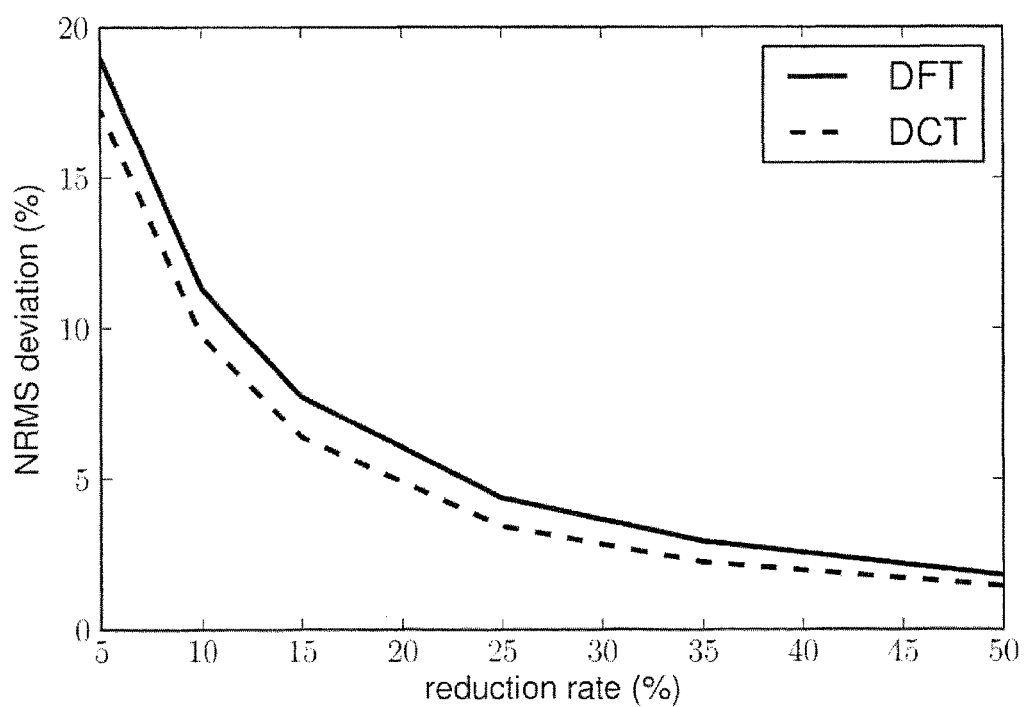
FIG. 2 shows the relative error of system matrices determined by means of the proposed method in comparison with a fully scanned system matrix, wherein the number of calibration measurements is between 5% and 50% of the full number of scanning points (N=2720). Up to a reduction to 10%, the error is below 10% and therefore in a tolerable range.
Figure 3:
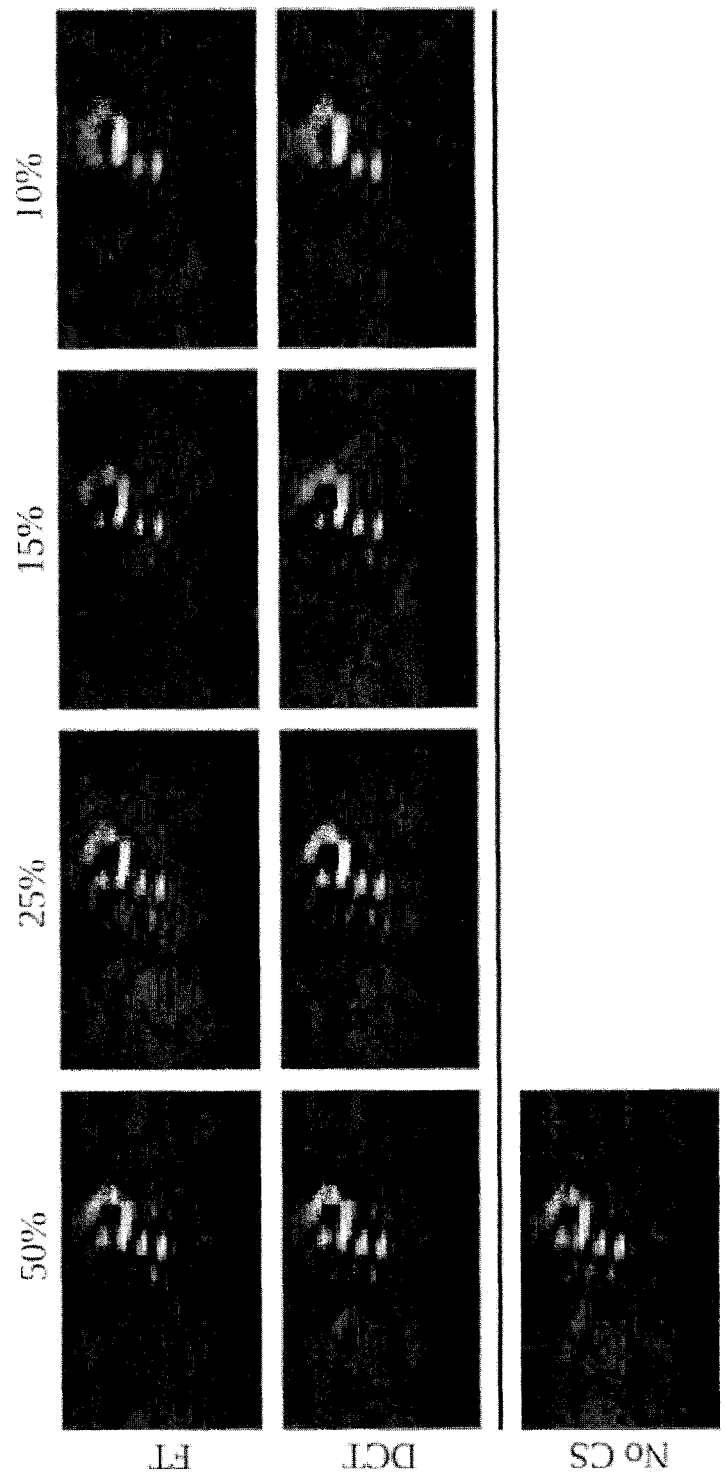
FIG. 3 shows reconstructed MPI data determined by the system matrices reconstructed by compressed sensing. A data set reconstructed with a fully scanned system matrix is used as reference. The reconstructed data shows no quality loss up to a reduction to 15%.

Variants and further advantageous properties and embodiments of the invention are described below.

One simple class of variants of the inventive method, which is based on conventional and currently used methods of prior art, is characterized in that the calibration sample is shifted within the volume under investigation to the locations of the M voxels and one calibration MPI measurement is performed in each case. These method variants can be easily performed using a measuring mechanism that is normally provided in conventional MPI apparatus.

In a further class of variants of the inventive method, the calibration sample may alternatively remain stationary during the calibration MPI measurements and the magnetic fields of the MPI apparatus may be varied in such a fashion that the static magnetic fields that prevail at the locations of the M voxels are reproduced, one after another. In this fashion, the relatively complex shifting mechanism can be omitted, in particular in MPI apparatus that are being newly produced and developed.

A third class of variants of the inventive method is characterized in that during the calibration MPI measurements, the calibration sample remains stationary and magnetic fields of a system calibration unit that is independent of the MPI apparatus are varied in such a fashion that the static magnetic fields that prevail at the locations of M voxels are reproduced, one after another. A dedicated system calibration unit can considerably improve the signal-to-noise ratio of the calibration measurement in comparison with a "normal" MPI apparatus.

In one preferred variant of the inventive calibration method, the volume of the calibration sample is larger than the volume of a voxel, thereby achieving a gain in signal intensity and therefore improving the signal-to-noise ratio of the calibration measurement, however, generally at the expense of the resolution.

In a further development of the above-mentioned method variant, the calibration sample may have a non-homogeneous inner structure in order to improve the signal-to-noise ratio of the calibration measurement without thereby deteriorating the resolution of the inventive method. It is e.g. feasible to configure the calibration sample from a number of voxels with intermediate spaces, wherein the intermediate spaces may contain non-magnetic material for stabilizing the calibration sample. Calibration samples that have a non-homogeneous structure and irregularly cover different voxels are also feasible.

The method presented by the present invention depends critically on suitable selection of the base transformation B. Different possibilities are presented below for this purpose:
- analytical transformations, such as e.g. Discrete Fourier Transformation (DFT), Discrete Cosine Transformation (DCT), Discrete Wavelet Transformation (DWT), or discrete Chebyshev Transformation (DTT). In case of mufti-dimensional imaging (2D/3D), the mufti-dimensional variants of the above-mentioned transformations can be utilized.
- a modelled MPI system matrix. Since a modeled MPI system matrix already has a considerably greater similarity to the real system matrix than the above-mentioned analytical transformation matrices, the sparsity can be increased, thereby reducing the number of calibration measurements that are required.
- a measured MPI system matrix. The scenario would be as follows: A highly resolved system matrix is measured. When, at a later point in time, the measurement parameters of the particle charge change, a new highly resolved system matrix can already be determined with only a few calibration measurements. This utilizes the fact that the system matrix changes only slightly in case the measurement parameters or particle charge change. After determination of the coefficients $v_k$ the full system matrix can be determined through evaluation of (4).

The advantages of the method proposed in the present invention depend substantially on the selection of the parameters N and M. For small N (<100), the effort of compressed sensing reconstruction of the system matrix is presumably not profitable. For larger values of N, M should be selected just in such a fashion that a good result can be achieved with a minimum number. The 2D data used in the application example achieved a very good result with a reduction to 10% of the calibration measurements. With other transformation matrices (simulated/measured system matrix), the number of required calibration measurements can presumably be further considerably reduced. In case of 3D measurements, the ratio between M and N can be selected to be still substantially smaller than for 2D measurements.

For this reason, M and N are selected in the inventive calibration method in such a fashion that the following applies:
$100 \leq N < 10^{12}$
and
$M/N \leq 0.5$, advantageously $M/N < 0.1$, in particular $M/N < 10^{-3}$.

For image reconstruction, the MPI imaging equation must be solved with a suitable method. While in this connection, the imaging matrix in the frequency region is normally considered, [GC11] proposed to consider the matrix in the time domain. Assuming idealized magnetic fields, the MPI imaging equation can thereby be written as a convolution. The "X-space" reconstruction method described in [GC11] provides an image with a relatively low resolution ("native resolution") by direct gridding or an image with high resolution through gridding with subsequent deconvolution. There are moreover very efficient algorithms for the direct solution of a convolution equation, which can then be utilized for MPI image reconstruction. A convolution kernel is required for the deconvolution approach or the direct solution of the convolution equation.

The method described in the present invention can also be utilized to determine this convolution kernel. For this purpose, the convolution kernel can be determined directly in the time domain by means of the described compressed sensing approach. In order to detect a spatial dependence of the convolution kernel, the kernel can be determined at different points in time of the trajectory. The information about the convolution kernel is also in the frequency based system function. In order to determine the convolution kernel, the system matrix determined in the frequency region must be transferred to the time domain. The matrix lines subsequently represent the convolution kernel which is spatially shifted in dependence on the line number and may possibly also be dependent on the location.

For this reason, one variant of the inventive calibration method is particularly preferred, which is characterized in that a convolution kernel, which can be spatially dependent, is determined from the created and stored image reconstruction matrix and used for improving the spatial resolution in the subsequent performance of an X space reconstruction.

The present invention also concerns MPI imaging methods which each include the performance of an MPI experiment and utilize an image reconstruction matrix which is created in accordance with the calibration method of the above-described type.

The invention also concerns an MPI apparatus for performing the calibration method and/or the MPI imaging method of the above-described type, which is characterized in that an electronic control unit is provided, in which a transformation matrix for sparsification of the image reconstruction matrix is stored for applying compressed sensing steps in the calibration method, wherein the control unit can perform a number of M<N calibration MPI measurements for M voxels and create therefrom the image reconstruction matrix and store it.

Parameter of the exemplary data of the embodiment illustrated in the figures

For evaluating the invention, 2D-MPI data were recorded which image a phantom filled with particles. The phantom consists of 12 points that represent the letter P. The FISTA algorithm [BT09] was used as compressed sensing method and the parameter $\epsilon$ was selected to obtain optimum results. The number of image points is 68×40 (N=2720). The measuring field covers a range of 20.4 mm×12 mm. The calibration sample consists of a cube having an edge length of 0.6 mm and, like the phantom, is filled with the tracer Resovist.

REFERENCES

[WGR09] J. Weizenecker, B. Gleich, J. Rahmer, H. Dahnke, and J. Borgert. Three-dimensional real-time in vivo magnetic particle imaging. Phys. Med. Biol., 54(5):L1-L10, 2009.

[KSB10] T. Knopp, T. F. Sattel, S. Biederer, J. Rahmer, J. Weizenecker, B. Gleich, J. Borgert, and T. M. Buzug.

Model-based reconstruction for magnetic particle imaging. IEEE Trans. Med. Imaging, 29(1):12-18, 2010.

[LDP07] M. Lustig, D. Donoho, J. M. Pauly. Sparse MRI: The application of compressed sensing for rapid MR imaging. Magn. Reson. Med. 2007 December; 58(6): 1182-95.

[Lam12] J Lampe et al. Fast reconstruction in magnetic particle imaging. *Phys. Med. Biol.* 2012, 57.

[HMC09] Hossein Mohimani, Massoud Babaie-Zadeh, Christian Jutten, "A fast approach for overcomplete sparse decomposition based on smoothed L0 norm", IEEE Transactions on Signal Processing, Vol. 57, No. 1, January 2009, pp. 289-301.

[BT09] Amir Beck, Marc Teboulle A Fast Iterative Shrinkage-Thresholding Algorithm for Linear Inverse Problems, SIAM Journal on Imaging Sciences (2009) Volume: 2, Issue: 1, Pages: 183

[HBRGB12] A. Halkola, T. Buzug, J. Rahmer, B. Gleich, and C. Bontus, "System calibration unit for magnetic particle imaging: Focus field based system function," in Springer Proceedings in Physics Volume 140, vol. 42, Lübeck, March 2012, pp. 27-31.

[GC11] P. W. Goodwill and S. M. Conolly, Multidimensional X-Space Magnetic Particle Imaging, IEEE Trans. Med. Imag., 30(9), 1581-1590, 2011.

I claim:

1. A method for calibrating an MPI apparatus for performing an MPI experiment of a volume under investigation, the method comprising the steps of:
   a) determining compressed sensing steps using a transformation matrix that sparsifies an image reconstruction matrix, the transformation matrix comprising analytic transformations, a modelled MPI-system matrix, a simulated or a measured system matrix;
   b) carrying out M calibration MPI measurements for M voxels of a calibration sample, the M voxels being selected in a random or pseudo-random fashion; and
   c) using the transformation matrix of step a) and the measurements of step b) to create and store an image reconstruction matrix with which signal contributions of N voxels within the volume under investigation are determined, wherein M<N.

2. The method of claim 1, wherein the calibration sample is shifted within the volume under investigation to locations of the M voxels and one calibration MPI measurement is performed for each voxel.

3. The method of claim 1, wherein the calibration sample remains stationary during the calibration MPI measurements and magnetic fields of the MPI apparatus are varied in such a fashion that static magnetic fields that prevail at locations of the M voxels are reconstructed, one after another.

4. The method of claim 1, wherein the calibration sample remains stationary during the calibration MPI measurements and magnetic fields of a system calibration unit that is independent of the MPI apparatus are varied in such a fashion that static magnetic fields that prevail at locations of the M voxels are reproduced, one after another.

5. The calibration method of claim 1, wherein a volume of the calibration sample is larger than a volume of a voxel.

6. The calibration method of claim 1, wherein the calibration sample has a non-homogeneous inner structure.

7. The calibration method of claim 1, wherein the transformation matrix includes Discrete Fourier Transformation (DFT), Discrete Cosine Transformation (DCT), Discrete Wavelet Transformation (DWT) or discrete Chebyshev Transformation (DTT), wherein, in case of multi-dimensional imaging, the multi-dimensional variants of those transformations are utilized.

8. The calibration method of claim 1, wherein the following applies: $100<N<10^{12}$ and $M/N<0.5$, $M/N<0.1$ or $M/N<10^{-3}$.

9. The calibration method of claim 1, wherein a convolution kernel, which can be spatially dependent, is determined from the created and stored image reconstruction matrix and used for improving a spatial resolution in subsequent performance of an X space reconstruction.

10. The method of claim 1, further comprising the steps of:
   d) carrying out an MPI experiment; and
   e) constructing an MPI image following step d) using the image reconstruction matrix that is created and stored in step c).

11. An MPI apparatus suitable for performing a calibration method, the MPI apparatus having an electronic control unit, wherein the electronic control unit comprises:
   means for determining compressed sensing steps using a transformation matrix that sparsifies an image reconstruction matrix, the transformation matrix comprising analytic transformations, a modelled MPI-system matrix, a simulated or a measured system matrix;
   means for carrying out M calibration MPI measurements for M voxels of a calibration sample, the M voxels being selected in a random or pseudo-random fashion; and
   means for using said transformation matrix and said M calibration MPI measurements in order to create and store an image reconstruction matrix with which signal contributions of N voxels within the volume under investigation are determined, wherein M<N.

12. The MPI apparatus of claim 11, further comprising:
   means for carrying out an MPI experiment; and
   means for constructing an MPI image using said image reconstruction matrix.

* * * * *